United States Patent [19]

Olerud et al.

[11] Patent Number: 4,625,718
[45] Date of Patent: Dec. 2, 1986

[54] AIMING APPARATUS

[75] Inventors: Sven E. Olerud, Laennholm, Sweden; Karl M. Richter, Wendtorf, Fed. Rep. of Germany

[73] Assignee: Howmedica International, Inc., Kiel, Fed. Rep. of Germany

[21] Appl. No.: 742,676

[22] Filed: Jun. 7, 1985

[30] Foreign Application Priority Data

Jun. 8, 1984 [DE] Fed. Rep. of Germany ... 8417428[U]

[51] Int. Cl.$^4$ ................................................ A61F 5/04
[52] U.S. Cl. ............................ 128/92 VD; 128/92 YY; 128/329 R
[58] Field of Search .............. 128/92 R, 92 EB, 92 E, 128/329 R, 303 B, 310, 317

[56] References Cited

U.S. PATENT DOCUMENTS 3,964,480  6/1976  Froning ........................... 128/303 B
4,336,805  6/1982  Smirmaul ........................ 128/310
4,485,815  4/1984  Amplatz .......................... 128/329 R
4,534,050  8/1985  Smith ............................. 128/303 B Primary Examiner—Gene Mancene
Assistant Examiner—C. W. Shedd
Attorney, Agent, or Firm—Charles J. Knuth; Peter C. Richardson; Lawrence C. Akers

[57] ABSTRACT

An aiming apparatus for making transverse bores in a patient's bone in register with the holes or bores of an osteosynthesis aid in the bone, especially an interlocking nail, comprises an elongated holder for the accommodation of an aiming member adapted to be brought into the beam path of an X-ray apparatus, a reception head for receivig a drill or wire drill rotatably supported in the holder, and a power drive supported by the holder for rotatably driving the reception head. The reception head is made of a material transparent to X-ray radiation.

8 Claims, 4 Drawing Figures

AIMING APPARATUS

BACKGROUND OF THE INVENTION

The present invention relates to an aiming apparatus for making transverse bores in bones in register with holes or bores of an osteosynthesis aid therein, especially an interlocking nail, comprising a holder for the accommodation of an aiming member adapted to be brought into the beam path of an X-ray apparatus.

Interlocking nails for the treatment of bone fractures, for instance, of the femur or the tibia, are fixed in the bone with the aid of transverse screws. In order that the transverse screws may be passed through the transverse bones in the interlocking nail, registered transverse bores must be made in the bone. It is that purpose the aiming apparatus serves.

An aiming apparatus has already become known comprising a an aiming head having a bore for the accommodation of an aiming sleeve and arranged at an elongated aiming head holding means in such a manner that it is adjustable longitudinally of the holding means (German utility model No. 78 05 301). The aiming head holding means is mounted in a fitting conntected to a source of x-ray radiation. The holding means is displaceably mounted in the fitting. The known aiming apparatus is connected to the x-ray apparatus and is dependent thereon. It has, therefore, also become known to provide a distal aiming apparatus which may be used independently of the type or make of the x-ray apparatus being used (German utility model) 82 08 970.1). With the known aiming apparatus a nail holding means is provided for the detachable accommodation of the proximal end of the interlocking nail approximately in parallel with the elongated aiming head holding means which in its turn is fitted at a holding arm displaceable about the axis of the interlocking nail in the nail holding means. The arm is detachably fitted at the aiming head holding means and is displaceable in a direction approximately in parallel with the nail axis in the aiming head holding means. Two adjusting pins may be received in the aiming head holding means vertically with respect to the axis of the interlocking nail. The known apparatus is distinguished for its relatively high grade aiming accuracy, indeed, but the handling thereof is very much time consuming. Besides, expenditure in terms of costs relating to the apparatus proper is considerable.

The invention is based upon the problem of providing a distal aiming apparatus which is distinguished for a simple and quick handling thereof in spite of a high grade aiming accuracy.

SUMMARY OF THE INVENTION

In accordance with the invention this problem is solved in that a reception head of a material transparent to x-ray radiation is rotatably supported in the holding means for the accommodation of a drill or a drill wire, and a powered driving machine is furthermore arranged at the holding means for rotatably driving the reception head.

The aiming apparatus according to the invention not only serves to detect the point where to perform the transverse bore in the bone but at the same time serves to make a preliminary bore. As the reception head for a drill or drill wire is transparent to the x-ray radiation, the drill appears as a point on the image screen. Said point is brought into register with a hole or transverse bore, respectively, of the interlocking nail in the process of aiming. This done, the drilling action is performed through the soft components and the bone with the aid of the drill or drill wire, respectively. Following this, the aiming apparatus is removed and the boring action is carried out via the drill wire or drill, respectively, with the aid of a hollow drill for the suitable bone screw. Following this, the drill wire or primary drill, respectively, is removed. It goes without saying that when using a drill wire or a suitable drill, respectively, in connection with the aiming apparatus, the diameter is relatively small so that the boring action may be performed with the aid of the hollow drill.

The aiming apparatus in accordance with the invention is distinguished for a relatively high aiming accuracy. It offers the advantage that a control may be carried out via an image screen still during the preliminary boring action.

It has already been mentioned that following the boring action with the aid of the drill wire the aiming apparatus must be detached from the drill wire. Provision is made for this purpose in one embodiment of the invention for the reception head to comprise a disc of synthetic material with an opening to detachably receive a clamping sleeve of synthetic material. The rotatably supported disc of synthetic material is transparent to x-ray radiation. The same is equally applicable to the detachable clamping sleeve which accommodates the drill wire. In a further embodiment of the invention provision is made in this connection for the the opening to be a polygonal shape and the clamping sleeve to have a corresponding outside configuration as well as a flange coming to lie in close contact against one side of the disc of synthetic material. The opening is the shape of a square, for example. The clamping sleeve has a corresponding outside configuration and is plugged into the opening so that upon rotation of the disc of synthetic material the clamping sleeve will be cammed along. The clamping sleeve is plugged into the opening on the side of the disc of synthetic material facing the patient, with the flange coming to lie in close contact against the disc of synthetic material during the boring action, so as to form an abutment for the axial pressure prevailing during the boring action.

The disc of synthetic material is then caused to rotate during the boring action. There are various possiblities of construction for a suitable drive of the disc of synthetic material. One possibility in accordance with the invention consists in that the disc of synthetic material is provided with a toothing formation on the periphery thereof. The toothing is in engagement with a suitable pinion which is in operatonal engagement with the shaft of the driving engine via an angular gear.

It may indeed by imagined to arrange the holding means for the aiming apparatus in a stationary apparatus for adjustment. However, handling the holding means freely is to be preferred. Provision is made for this purpose in one embodiment of the invention for the holding means to comprise an elongated sheet metal member and the reception head to be mounted approximately centrally in a bearing housing. The sheet metal member may consist of aluminum and have a length of 50 to 60 cm. Such a length is sufficient to keep the hands of the operator outside the immediate range of radiation of the x-ray source.

In a further embodiment of the invention the sheet metal member comprises a clamping device for the housing of a pneumatic or electric driving engine. The driving engine may be a usual type of pneumatically or electrically or battery operated driving engine in the form of a gun adapted to be fastened in clamping engagement with its housing at the sheet metal member. It goes without saying that also a special motor may be used. In the case of the gun type driving engine the gun handle may at the same time form a handling means at one end of the sheet metal member.

DETAILED DESCRIPTION OF THE INVENTION

The invention will now be described in more detail by way of drawings.

Figures 1, 2:
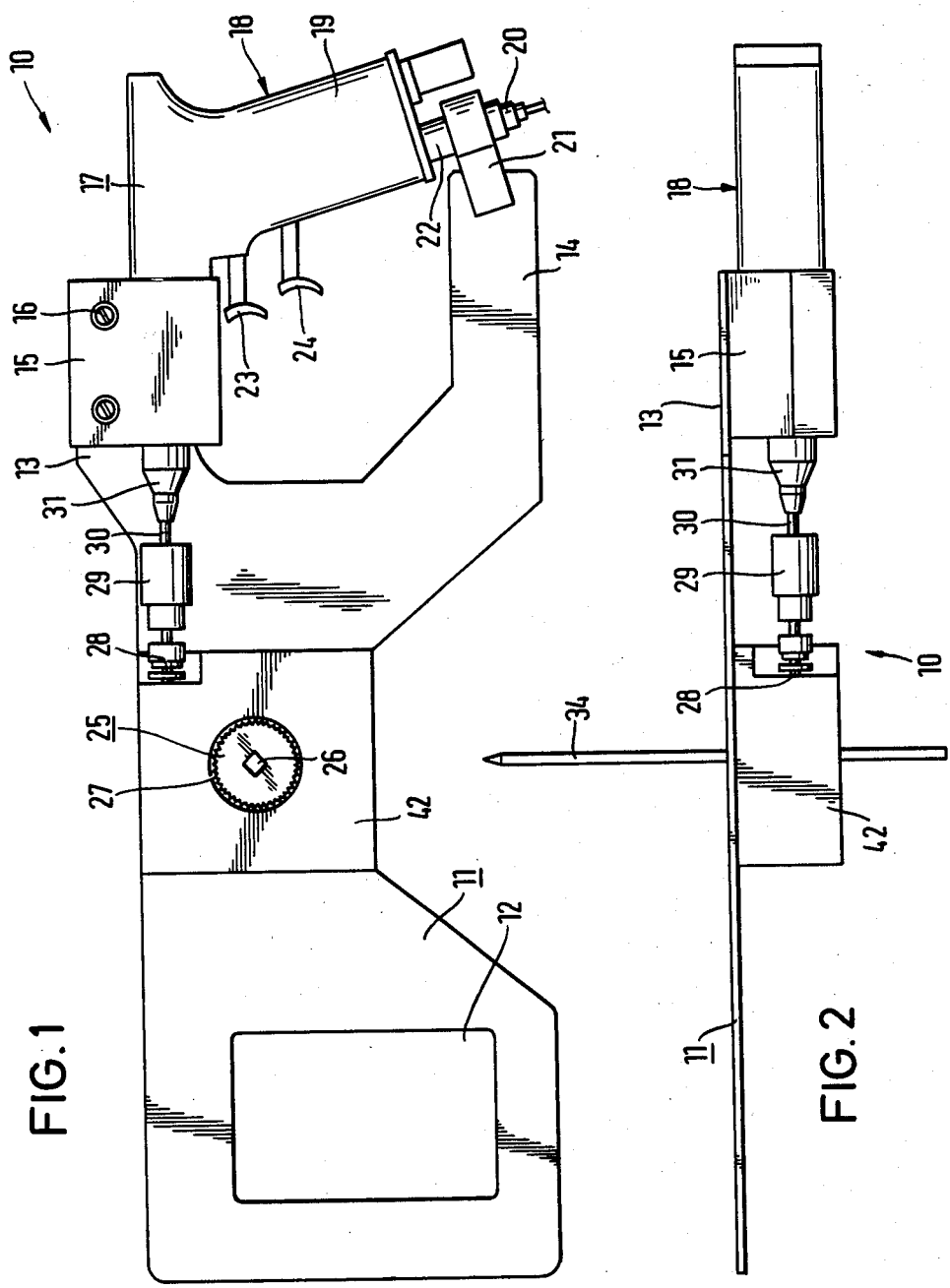
FIG. 1 shows a lateral view of an aiming apparatus according to the invention.
FIG. 2 shows a top plan view taken on the aiming apparatus according to FIG. 1.

Prior to enlarging in more detail on the individual representations shown in the drawings, it is to be stated that each of the components described is of inventively essential importance by itself or in connection with features of the claims.

The aiming apparatus generally designated at 10 comprises a holding sheet metal member 11 of aluminum having a thickness of 5 mm said sheet metal member being enlarged at the ends thereof like a handle. The length of the sheet metal member 11 is about 50 to 60 cm with a handling opening 12 formed at the left-hand end thereof. Two legs 13, 14 are formed in parallel at the right-hand end. The upper leg 13 comprises a bipartite clamping block 15 with screws 16, said screws 16 clamping the two members of the block 15 against each other. The member of the clamping block closest to the leg 13 is fastened in a suitable manner. The clamping block 15 serves for the accommodation of the housing of a gun type driving engine 18. The driving engine 18 is pneumatically operated and comprises a spout 20 at the lower end of the gun handle 19 for communication with a compressed air hose. Connected to the lower leg 14 of a slightly longer length is a fastened clip 21 which clamps the pipe connection 22 comprising the spout 20. The gun handle 19 which is provided with two releasing means 23, 24 projecting into the opening between the legs 13, 14 thus forms at the same time a handling means for the sheet metal member 11.

Fitted in the medium narrower range of the sheet metal member 11 is a bearing housing 24 to the same side as the clamping block 15. In the bearing housing 24, a disc 25 of synthetic material is supported in axially fixed relationship but to be capable of rotation, said disc being provided with an opening 26 in the shape of a square. The circumference of the disc 25 of synthetic material is provided with a tooth formation 27. Said tooth formation 27 is in enagagement with a driving pinion (not shown) of an angular gear (not shown) which is supported in the bearing housing 24. The input shaft 28 of the angular gear is connected to a shaft portion 29 which is in connection with the spindle 30 of the pneumatic driving engine 18. The spindle 30 projects from the nose portion 31 of the housing 17.

Figure 3:
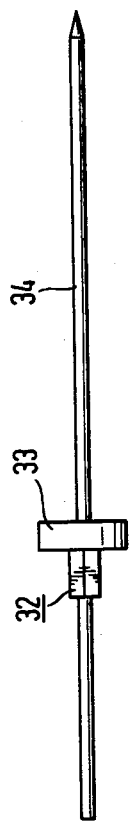
FIG. 3 shows a drill wire with a clamping sleeve for an aiming apparatus according to FIG. 1.

FIG. 3 shows in a lateral view a clamping sleeve 32 of rectangular cross section, which is provided with a flange 33 at one end thereof. The clamping sleeve 32 and the flange 33 are likewise made of synthetic material. The clamping sleeve 32 serves to clampingly accommodate a drill wire 34. As will be seen from FIG. 2, the clamping sleeve 32 is inserted into the opening 26 of the disc of synthetic material 25 on the side facing away from the bearing housing 24, with the flange 33 coming to lie in close contact against the outer surface of the disc 25.

Figure 4:
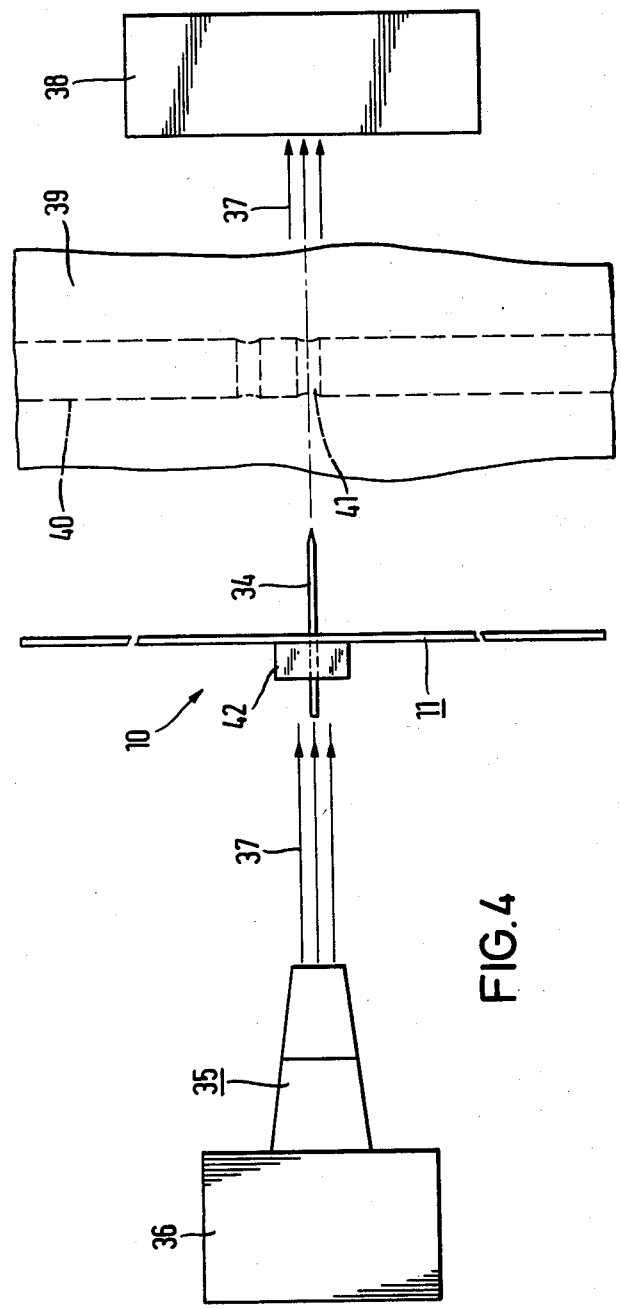
FIG. 4 shows in a diamgrammatic view the build-up of an x-ray system with an aiming apparatus according to the invention.

FIG. 4 shows in a diagrammatic view a source of x-ray radiation 35 which is arranged at a suitable holding means 36. Situated in the beam path 37 of the x-ray source is a receiver 38. The receiver is connected to an image screen (not shown). The leg 9 of a patient, for example, is arranged in the beam path 37 of the x-ray source 35, with an interlocking nail 40 (shown in broken lines) present in the leg, which has been beaten in before. The interlocking nail 40 is provided with transverse bores 41. When the aiming apparatus 20 is held in the beam path 32, the wire drill 34 will form a picture of itself on the image screen in the form of a point. It may thus be brought into register with a transverse bore 41 likewise becoming visible on the image screen by manipulation of the sheet metal member 11 seizing it at both ends thereof. After the alignment has been completed a bore is made with the aid of the drill wire 34 through soft portions and the bone. Upon completion of said bore the aiming apparatus 10 is removed, with the drill wire 34 remaining in the leg. Following this, the final bore for a bone screw is made around the drill wire 34 with the aid of a hollow drill.

We claim:

1. An aiming apparatus for use in making transverse bores in a patient's bone in register with the holes of an osteosynthesis aid in the bone, such as an interlocking nail, said aiming apparatus comprising a holding means for the accommodation of an aiming member adapted to be brought into the beam path of an X-ray device, a reception head made of a material transparent to X-ray radiation and adapted to receive a drill or wire drill, said reception head being rotatably supported in the holding means, and a power drive means supported by said holding means to drive the reception head for rotation.

2. An aiming apparatus of claim 1 wherein the reception head comprises a disc made of synthetic material and provided with an opening for detachably receiving a clamping sleeve, said clamping sleeve being adapted to accommodate said drill or wire drill.

3. An aiming apparatus of claim 2 wherein said opening is polygonal in shape and said clamping sleeve has a corresponding outer configuration, with said clamping sleeve comprising a flange adapted to lie in close contact against one side of said disc.

4. An aiming apparatus of claim 2 wherein said disc is provided with a tooth formation on its periphery.

5. An aiming apparatus of claim 1 wherein said holding means comprises an elongated metal sheet member and said reception head is supported approximately centrally in a bearing housing which is fitted on one side of said metal sheet member.

6. An aiming apparatus of claim 5 wherein a clamping means for the housing of said power drive means is provided on said metal sheet member.

7. An aiming apparatus of claim 6 wherein said disc is provided with a tooth formation on its periphery, and said bearing housing comprises a reversing gear having a pinion in meshing engagement with said disc and being operatively connected to said power drive means.

8. An aiming apparatus according to claim 5 wherein said metal sheet member is provided with a handle at one end thereof.

* * * * *